United States Patent [19]

Morita et al.

[11] Patent Number: 4,963,684
[45] Date of Patent: Oct. 16, 1990

[54] PROCESS FOR PREPARING COTARNINE

[75] Inventors: Yoshiharu Morita, Yokohama; Naoshi Imaki, Atsugi; Tadashi Shirasaka, Machida; Tetsuro Shimpuku, Yokohama, all of Japan

[73] Assignee: Mitsubishi Kasei Corporation, Tokyo, Japan

[21] Appl. No.: 307,247

[22] Filed: Feb. 7, 1989

Related U.S. Application Data

[63] Continuation of Ser. No. 901,368, Aug. 28, 1986, abandoned.

[30] Foreign Application Priority Data

Sep. 11, 1985 [JP] Japan .................. 60-201075

[51] Int. Cl.$^5$ .................................. C07D 491/056
[52] U.S. Cl. .................................. 546/90; 514/291
[58] Field of Search .................................. 546/90

[56] References Cited

FOREIGN PATENT DOCUMENTS 0214051  3/1987 European Pat. Off. .............. 546/90
0214905  3/1987 European Pat. Off. .............. 546/90

OTHER PUBLICATIONS

Journal of the Chemical Society, Perkin Transactions I, 1974, pp. 1911-1920; A. H. Jackson et al.: "Phenol Oxidation. Part III. Synthesis of the Benzylisoquinoline Alkaloid Cularine", *p. 1912, left-hand column, lines 34-42; p. 1912, right-hand column, formulae 8,9.*
M. Shamma: "The Isoquinoline Alkaloids", 1972, chapter 19, pp. 359-362, Academic Press, New York, U.S., *Chapter 19, pp. 360-362; in particular p. 361, scheme II.*

Primary Examiner—Alan L. Rotman
Attorney, Agent, or Firm—Oblon, Spivak, McClelland, Maier & Neustadt

[57] ABSTRACT

A process for preparing cotarnine is provided which comprises oxidizing the amino group of a tetrahydroisoquinoline compound represented by the following formula (I):

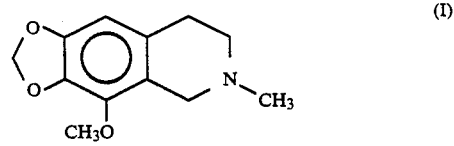

(I)

to convert said compound into a dihydroisoquinolinium salt represented by the following formula (II):

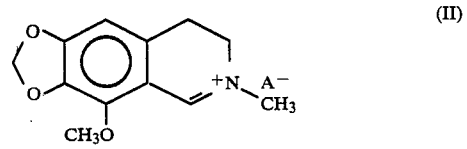

(II)

wherein A$^-$ represents an anion, and then hydrolyzing said dihydroisoquinolinium salt.

11 Claims, No Drawings

PROCESS FOR PREPARING COTARNINE

This application is a continuation of application Ser. No. 06/901,368, filed on Aug. 28, 1986, now abandoned.

This invention relates to a process for preparing cotarnine, a main starting material for the production of tritoqualine which has pharmacological activity, for example, as an anti-allergic agent as disclosed in Japanese Patent Application laid open Nos. 59-44374 and 59-44382. These laid open applications disclose the synthesis of tritoqualine from cotarnine by reacting cotarnine with a nitrophthalide compound thereby forming as an intermediate, 2-methyl-6,7-methylene dioxy-8-methoxy-1-[4,5,6-triethoxy-7-nitro-phthalidyl-(3)]-1,2,3,4 tetrahydroisoquinoline. The nitro group of the intermediate is then reduced to form tritoqualine as the desired product.

There has been known a method of synthesizing cotarnine by the oxidization of noscapine, one of alkaloids: Yakugaku Zasshi, Vol. 50, 559 (1930).

On the other hand, another synthetic method of cotarnine has also been known which comprises formylating 2-(3-methoxy-4,5-methylenedioxyphenyl)ethylamine, cyclizing, and N-methylating to prepare dihydroisoquinolinium salt: Ann., 395, 328 (1912).

In the former method described above, however, the starting material noscapine is expensive and has a problem in view of constant supply since it is derived from natural sources. On the other hand, in the latter method, an isomer may be formed in the cyclizing step and impurities derived from the isomer may be introduced into the final product cotarnine, resulting in a serious problem in the separation and purification of the product.

The present inventors have now found a new process for preparing cotarnine without forming such an isomer.

The present invention provides a process for preparing cotarnine which comprises oxidizing the amino group of a tetrahydroisoquinoline compound represented by the following formula (I):

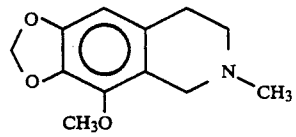

(I)

into a dihydroisoquinolinium salt represented by the following formula (II):

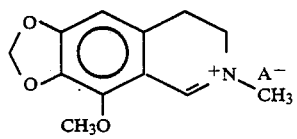

(II)

wherein $A^-$ represents an anion, and then hydrolyzing said dihydroisoquinolinium salt.

This invention will now be described more specifically.

Oxidizing agents used in the oxidization of the amino group of the tetrahydroisoquinoline compound represented by the formula (I) may include so-called halogenating agents, for example, halogens such as $Cl_2$, $Br_2$ and $I_2$; hypohalogenous acids and salts thereof such as NaOCl, NaOBr, NaOI, $Ca(OCl)_2 \cdot nH_2O$, ClOH and BrOH; and N-bromosuccinimide and N-chlorosuccinimide, with halogens being particularly preferred.

In the foregoing formula (II), $A^-$ represents an anion of such a halogenating agent.

Such an oxidizing agent may be used in an amount of from 0.1 to 10 moles, and preferably from 0.5 to 2 moles, per mole of the tetrahydroisoquinoline compound (I).

A base may promote the reaction when used in combination with the oxidizing agent.

The base may include, for example, a salt of an organic carboxylic acid such as $CH_3COOK$, $CH_3COONa$, $(CH_3COO)_2Ca$, $C_2H_5COOK$, $C_2H_5COONa$, $C_6H_5COOK$ or $C_6H_5COONa$; a metal alkoxide such as $CH_3ONa$, $CH_3OK$, $C_2H_5ONa$, $C_2H_5OK$, t-BuONa or t-BuOK; and a carbonate salt such as sodium carbonate, potassium carbonate or calcium carbonate. It may be used in an amount of from 0.1 to 10 moles, and preferably from 0.5 to 2 moles, per mole of the tetrahydroisoquinoline compound (I).

Although there is no particular restriction on reaction solvents, those inactive to the oxidization reaction are preferable and may include, for example, alcohols such as methanol, ethanol, isopropyl alcohol, butyl alcohol and t-butyl alcohol; carboxylic acids such as acetic acid and propionic acid; ethers such as diethyl ether, di-n-butyl ether, tetrahydrofuran and dioxane; hydrocarbons such as pentane, hexane, benzene and toluene; and halogenated hydrocarbons such as dichloromethane, chloroform and tetrachloromethane.

Such a solvent may be used in an amount of from 0.1 to 1000 ml, and preferably from 1 to 100 ml, per g of the tetrahydrosioquinoline compound (I).

The reaction temperature for the oxidization reaction may range from $-30°$ to $120°$ C., and preferably from $0°$ to $100°$ C.

After the oxidizing reaction is over, isolation and purification of the product dihydroisoquinolinium salt (II) may be carried out in any conventional manner in the field of organic chemistry. Alternatively, the product dihyroisoquinolinium salt (II) thus obtained may be subjected directly to the subsequent hydrolysis without being isolated, so as to obtain the final product cotarnine.

The hydrolysis is preferably carried out in the presence of a base which may include, for example, a salt of an organic carboxylic acid such as $CH_3COOK$, $CH_3COONa$, $(CH_3COO)_2Ca$, $C_2H_5COOK$ or $C_2H_5COONa$; a metal alkoxide such as $CH_3ONa$, $CH_3OK$, $C_2H_5ONa$, $C_2H_5OK$, t-BuONa or t-BuOK; a metal hydroxide such as sodium hydroxide, potassium hydroxide or calcium hydroxide; and a carbonate salt such as sodium carbonate, potassium carbonate or calcium carbonate.

Preferably, the base may be used in an amount of from 1 to 100 moles per mole of the dihydroisoquinolinium salt (II).

While any solvent inactive to the hydrolysis reaction may be used, water or an alcohol such as methanol, ethanol, propanol or isopropyl alcohol is preferable. Such a solvent is preferably used in an amount of from 0.1 to 1000 ml, and preferably from 1 to 100 ml, per g of the dihydroisoquinolinium salt (II).

The reaction temperature for the hydrolysis may preferably range from $-20°$ to $100°$ C.

After the hydrolysis reaction is over, deposited crystals are filtered out to obtain the desired product cotarnine.

The tetrahydroisoquinoline compound represented by the formula (I) is known (Yakugaku Zasshi, 50, 559 (1930)) and may be synthesized in accordance with the following reaction scheme, using as a starting material 2-methoxy-3,4-methylenedioxybenzaldehyde which may in turn be easily prepared by the known method (J. Chem. Soc. Perkin Trans. I, 1984, 709).

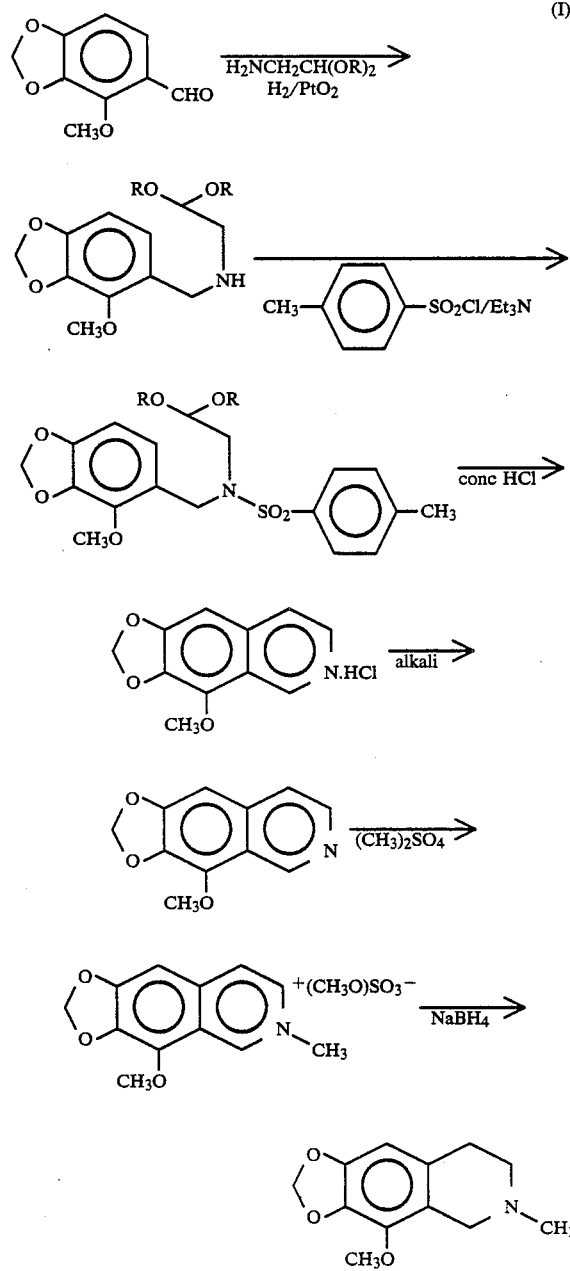

(R represents a lower alkyl group)

EXAMPLES

This invention will now be described more specifically with reference to the following examples but these examples are not to be construed as limiting the scope of the invention.

REFERENCE EXAMPLE 1

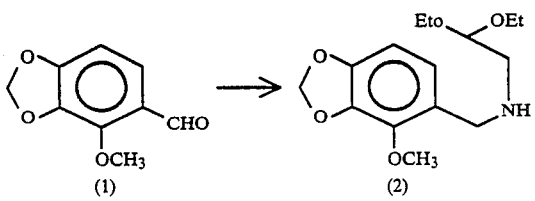

Platinum oxide was added in an amount of 1.0 g to 100 ml of ethanol, and hydrogen gas was passed through the mixture with stirring for 30 minutes. Then, 54.06 g (0.3 mol) of 2-methoxy-3,4-methylenedioxybenzaldehyde (1) and 40.78 g (0.3 mol) of aminoacetaldehyde diethylacetal (98% purity) in 100 ml of ethanol were added and hydrogenation was carried out while stirring the reaction mixture at room temperature for 8.5 hours. The catalyst was then removed by filtration and the solvent was distilled off at reduced pressure to obtain 89.43 g of N-(2-methoxy-3,4-methylenedioxybenzyl)aminoacetaldehyde diethylacetal (2) as an oil with 100% yield. IR and NMR of the resultant product are listed below.

IR (neat, νmax cm−1): 1630, 1495, 1465, 1255
$^1$H-NMR (60 MHz in CDCl$_3$, δppm):

| |
|---|
| 1.18 (6H, t, J=7Hz, —OCH$_2$C$\underline{H}_3$ × 2), |
| 1.88 (1H, s, —N$\underline{H}$), |
| 2.68 (2H, d, J=6Hz, NC$\underline{H}_2$CH(OEt)$_2$, |
| 3.3–3.9 (4H, m, —OC$\underline{H}_2$CH$_3$ × 2), |
| 3.70 (2H, s, ArC$\underline{H}_2$N), |
| 3.99 (3H, s, OC$\underline{H}_3$), |
| 4.58 (1H, t, J=6Hz, NCH$_2$C$\underline{H}$(OEt)$_2$), |
| 5.87 (2H, s, C$\underline{H}_2$⟨O/O⟩) |
| 6.42 (1H, d, J=8Hz,<br>6.70 (1H, d, J=8Hz, ⟨structure⟩ |

REFERENCE EXAMPLE 2

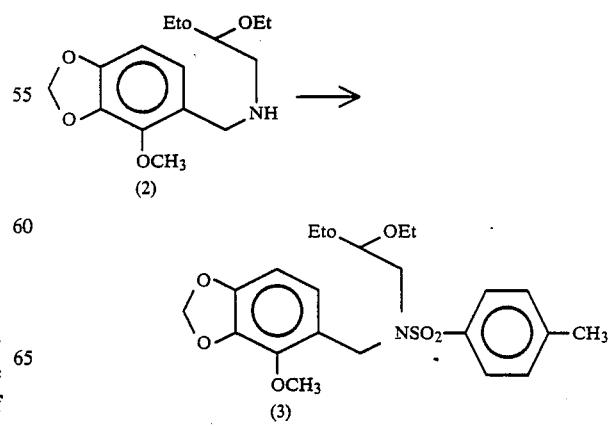

N-(2-methoxy-3,4-methylenedioxybenzyl-)aminoacetaldehyde diethylacetal (2) in an amount of 59.46 g (0.2 mol) and triethylamine in an amount of 28.45 ml (0.204 mol) were dissolved in 100 ml of methylene chloride, to which 38.88 g (0.204 mol) of p-toluenesulfonyl chloride in 80 ml of methylene chloride was added dropwise at 15°–30° C. over 25 minutes After stirring the mixture at room temperature for 30 minutes, 150 ml of water was added and the reaction mixture was stirred. The methylene chloride layer was separated from the aqueous layer and further washed with 100 ml of water. After drying the methylene chloride layer over anhydrous magnesium sulfate, the solvent was distilled off at reduced pressure to obtain 90.3 g of N-(2-methoxy-3,4-methylenedioxybenzyl)-N-(p-toluenesulfonyl)aminoacetaldehyde diethylacetal (3) as an oil. Yield: 100%. IR and NMR of the resultant product are listed below.

IR (neat, νmax cm⁻¹): 1470, 1340, 1265, 1160, 1070
¹H-NMR (60 MHz in CDCl₃, δppm ):

1.13 (6H, t, J=7Hz, OCH₂C$\underline{H}$₃ × 2)

2.40 (3H, s, SO₂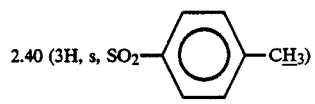CH₃)

3.2–3.8 (6H, m, $\begin{matrix}OC\underline{H}_2CH_3 \times 2 \\ NC\underline{H}_2CH(OEt)_2\end{matrix}$ )

3.82 (3H, s, —OCH₃)
4.43 (2H, s, ArC$\underline{H}$₂N)
4.58 (1H, t, J=5Hz, NCH₂C$\underline{H}$(OEt)₂)

5.83 (2H, s, C$\underline{H}$₂$\langle$ $\begin{matrix}O— \\ O—\end{matrix}$ )

6.40 (1H, d, J=8Hz,
6.77 (1H, d, J=8Hz, 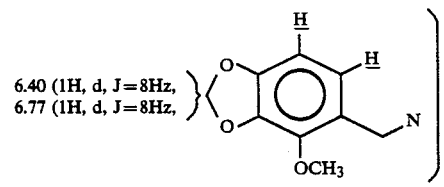 )

7.18 (2H, d, J=8Hz, 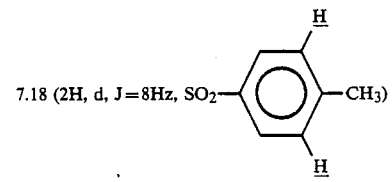 )

7.58 (2H, d, J=8Hz, 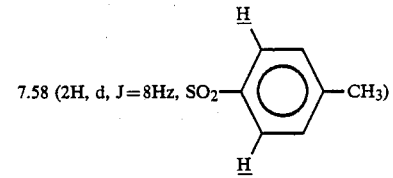 )

REFERENCE EXAMPLE 3

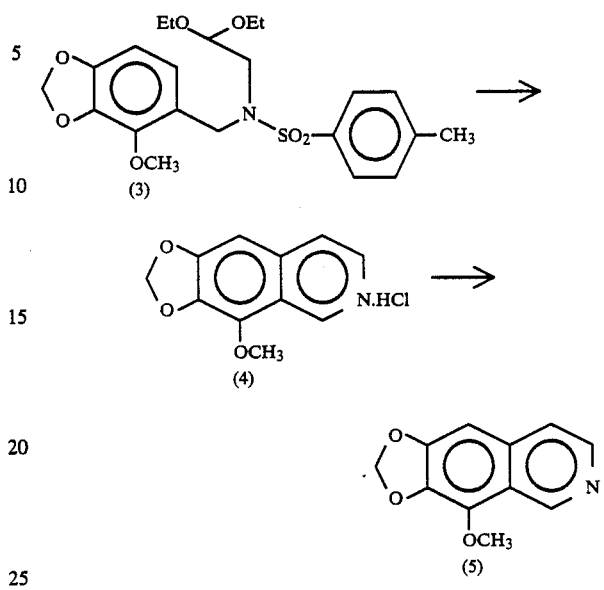

N-(2-methoxy-3,4-methylenedioxybenzyl)-N-(p-toluenesulfonyl)aminoacetaldehyde diethylacetal (3) in an amount of 69.89 g (0.155 mol) was dissolved in 0.194 ml of dioxane, to which 14.7 ml (0.169 mol) of concentrated hydrochloric acid and 47.1 ml of water were added and heated under reflux for two hours and 40 minutes. After the mixture were cooled to about 5° C., deposited crystals were collected by filtration, washed with 30 ml of cold dioxane and then dried to obtain 22.95 g of 8-methoxy-6,7-methylenedioxyisoquinoline hydrochloride (4) as yellow crystals. Yield 61.8%.

17.8 g (74.3 mmol) of the compound (4) thus obtained was added to 50 ml of water, which was then incorporated with 100 ml of methylene chloride and rendered basic with 25% aqueous solution of sodium hydroxide under water-cooling. After the solution was separated into two layers, the aqueous layer was extracted with 20 ml of methylene chloride. Then, the methylene chloride layers were combined and washed with 30 ml of water. They were dried over anhydrous magnesium sulfate and then concentrated at reduced pressure to obtain 15.06 g of 8-methoxy-6,7-methylenedioxyisoquinoline (5) with a yield of 99.7%. The resultant product was recrystallized from ethyl acetate/n-hexane: m.p. 144°–5° C. IR and NMR of the resultant product are listed below.

IR (KBr, νmax cm⁻¹): 1595, 1460, 1040
¹H-NMR (60 MHz in CDCl3, δppm):

4.17 (3H, s, OC$\underline{H}$₃)

5.97 (2H, s, C$\underline{H}$₂$\langle$ $\begin{matrix}O— \\ O—\end{matrix}$ )

6.72 (1H, s, 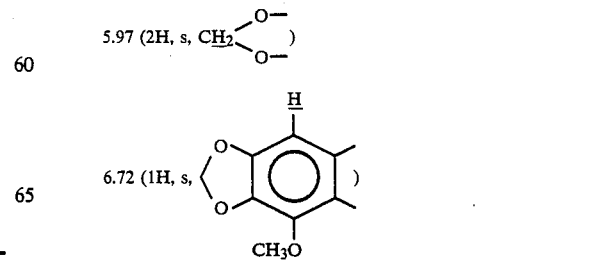 )

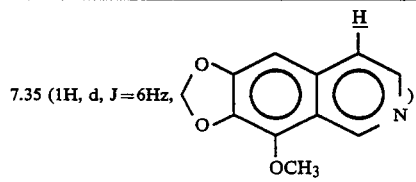
7.35 (1H, d, J=6Hz, ...)

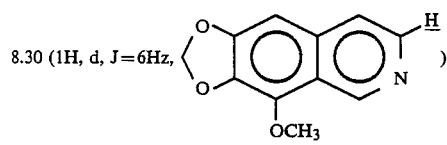
8.30 (1H, d, J=6Hz, ...)

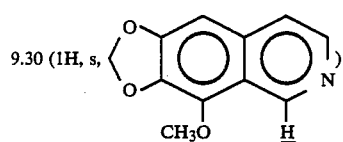
9.30 (1H, s, ...)

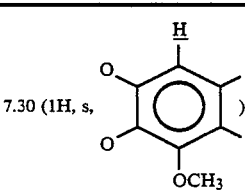
7.30 (1H, s, ...)

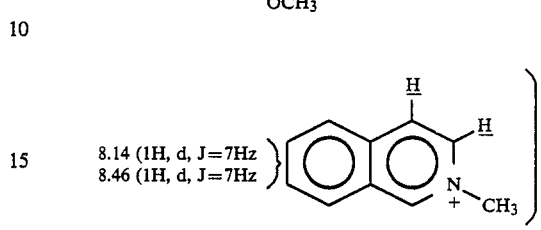
8.14 (1H, d, J=7Hz)
8.46 (1H, d, J=7Hz)

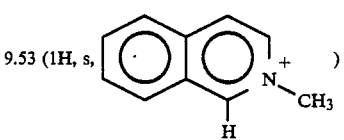
9.53 (1H, s, ...)

REFERENCE EXAMPLE 4

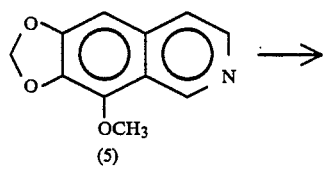

REFERENCE EXAMPLE 5

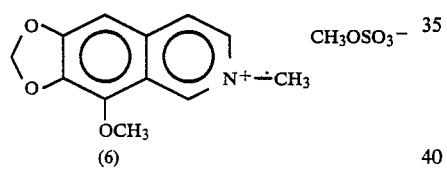

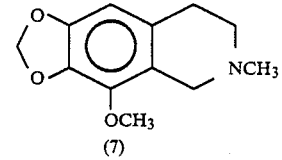

8-Methoxy-6,7-methylenedioxyisoquinoline (5) in an amount of 2.03 g (10 mmol) was dissolved into 40 ml of toluene while heating them at 60° C. Then, 1.13 ml (12 mmol) of dimethyl sulfate was added and stirred at 60° C. for 4 hours. After cooling, deposited crystals were collected by filtration, washed with toluene and then dried to obtain 3.30 g of 8-methoxy-2-methyl-6,7-methylenedioxyisoquinolinium methyl sulfate (6) with a yield of 100%. The resultant product was then recrystallized from ethanol: m.p. 172°–4° C. IR and NMR of the resultant product are listed below.

IR (KBr, $\nu$max cm$^{-1}$) 1460, 1250, 1230, 1055, 1010

$^1$H-NMR (60 MHz in CDCl$_3$ DMS-d$_6$ $\delta$ppm)

3.47 (3H, s, C$\underline{H}_3$OSO$_3^-$)

4.27 (3H, s, OC$\underline{H}_3$)
4.42 (3H, s, N—C$\underline{H}_3$)

6.33 (2H, s, C$\underline{H}_2$(O—)(O—))

8-Methoxy-2-methyl-6,7-methylenedioxyisoquinolinium methyl sulfate (6) in an amount of 1.47 g (4.47 mmol) was dissolved in 20 ml of water, to which 0.34 g (9 mmol) of sodium boron hydride was portionwise added under cooling with water. After stirring the mixture for two hours, 10 ml of methylene chloride was added and the solution was rendered acidic with concentrated hydrochloric acid. The solution was separated and the methylene chloride layer was extracted with 2N hydrochloric acid. The aqueous layers were combined and rendered basic with 25% aqueous solution of sodium hydroxide. This was extracted with 15 ml and then 10 ml of methylene chloride successively, washed with 10 ml of water, and dried over anhydrous magnesium sulfate. The solvent was distilled off to obtain 780 mg of 8-methoxy-2-methyl-6,7-methylenedioxy-1,2,3,4-tetrahydroisoquinoline (7) (hydrocotarnine) with a yield of 79%.

EXAMPLE 1

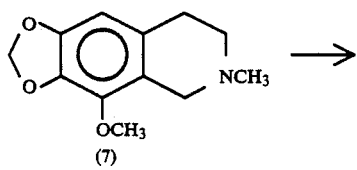
(7)

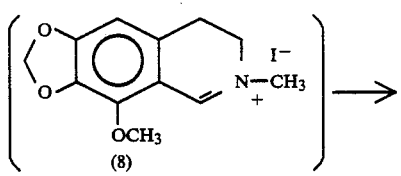
(8)

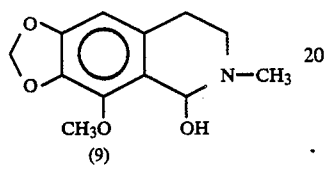
(9)

8-Methoxy-2-methyl-6,7-methylenedioxy-1,2,3,4-tetrahydroisoquinoline (7) in an amount of 221 mg (1 mmol) and potassium acetate in an amount of 108 ml (1.1 mmol) were dissolved in 2 ml of ethanol, to which 254 mg (1 mmol) of iodine in 2.4 ml of ethanol was dropwise added over 85 minutes while heating to about 75° C. After heating at 75° C. for 100 minutes, ethanol was distilled off at reduced pressure, 6 ml of water was added to the residue, and then 0.6 ml of 25% aqueous solution of sodium hydroxide was added under ice-cooling. After stirring at room temperature for 30 minutes, crystals were collected by filtration, washed with 2×0.6 ml of water and then dried to obtain 217 mg of cotarnine (9) with 91% yield.

EXAMPLE 2

Reaction was carried out quite in the same manner as in Example 1 except for using bromine instead of iodine in Example 1 to obtain cotarnine with a yield of 55%.

As seen from the foregoing examples, it is possible according to the other process of this invention to prepare efficiently cotarnine, which is a main starting material for the production of tritoqualine useful as a pharmaceutical.

What we claim is:

1. A process for preparing cotarnine of the formula:

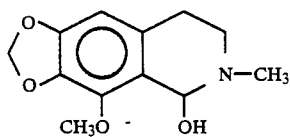

which comprises:
reacting from 0.1 to 10 moles of an oxidizing agent selected from the group consisting of a halogen, a hypohalogenouos acid and salts thereof, N-bromosuccinimide and N-chlorosuccinimide, which is a halogenating agent, with 1 mole of a tetrahydroisoquinoline compound of the formula:

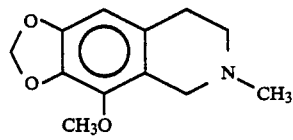

in a solvent selected from the group consisting of alcohols, carboxylic acids, ethers, hydrocarbons and halogenated hydrocarbons, thereby oxidizing said tetrahydroisoquinoline compound to a dihydroisoquinolinium cation of the formula:

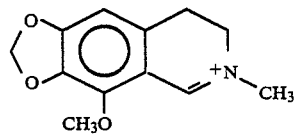

and
hydrolyzing said dihydroisoquinolinium cation by reacting 1 mole of said cation with from 1 to 100 moles of a base selected from the group consisting of the salt of an organic carboxylic acid, a metal alkoxide, a metal hydroxide and a carbonate salt at a temperature ranging from −20° to 100° C. in a solvent.

2. The process according to claim 1 wherein the halogenating agent is a halogen selected from the group consisting of $Cl_2$, $Br_2$ and $I_2$.

3. The process according to claim 1 wherein the halogenating agent is a hypohalogenous acid or salt thereof selected from the group consisting of NaOCl, NaOBr, NaOI, $Ca(OCl)_2.nH_2O$, ClOH and BrOH.

4. The process according to claim 1 wherein the halogenating agent is N-bromosuccinimide or N-chlorosuccinimide.

5. The process according to claim 1, wherein, in said hydrolysis of said dihydroisoquinolinium cation, said carboxylic acid salt is potassium acetate, sodium acetate, calcium acetate, potassium propionate or sodium propionate; said metal alkoxide is sodium methoxide, potassium methoxide, sodium ethoxide, potassium ethoxide, sodium t-butoxide or potassium t-butoxide; said metal hydroxide is sodium hydroxide, potassium hydroxide or calcium hydroxide; and said carbonate salt is sodium carbonate, potassium carbonate or calcium carbonate.

6. The process according to claim 1, wherein the solvent of the hydrolysis step is water or an alcohol.

7. The process according to claim 1, wherein said solvent in the hydrolysis step is employed in an amount ranging from 0.1 to 1000 ml per gram of said dihydroisoquinolinium cation.

8. The process according to claim 1, wherein the temperature of said oxidation reaction ranges from −30° to 120° C.

9. The process according to claim 1, wherein the solvent is present in said oxidation reaction in an amount ranging from 0.1 to 1000 ml per gram of said tetrahydroisoquinoline compound.

10. The process according to claim 1, wherein in said oxidation step, a base is present which is an organic carboxylic acid salt, a metal alkoxide, or a carbonate salt.

11. The process according to claim 10, wherein the amount of said base ranges from 0.1 to 10 moles per mole of said tetrahydroisoquinoline compound.

* * * * *